(12) United States Patent
Roberts

(10) Patent No.: US 9,360,850 B2
(45) Date of Patent: Jun. 7, 2016

(54) MODULAR MONITOR AND CONTROL SYSTEM FOR CELL SORTER STREAM

(71) Applicant: Rutgers, The State University of New Jersey, New Brunswick, NJ (US)

(72) Inventor: Arthur I. Roberts, Basking Ridge, NJ (US)

(73) Assignee: RUTGERS, THE STATE UNIVERSITY OF NEW JERSEY, New Brunswick, NJ (US)

(*) Notice: Subject to any disclaimer, the term of this patent is extended or adjusted under 35 U.S.C. 154(b) by 18 days.

(21) Appl. No.: 14/552,686

(22) Filed: Nov. 25, 2014

(65) Prior Publication Data

US 2015/0146962 A1    May 28, 2015

Related U.S. Application Data

(60) Provisional application No. 61/908,348, filed on Nov. 25, 2013.

(51) Int. Cl.
| | | |
|---|---|---|
| *G06K 9/00* | (2006.01) | |
| *G05B 15/02* | (2006.01) | |
| *B07C 5/342* | (2006.01) | |
| *G05D 7/06* | (2006.01) | |
| *G01N 15/14* | (2006.01) | |

(52) U.S. Cl.
CPC ............ *G05B 15/02* (2013.01); *B07C 5/3422* (2013.01); *G01N 15/1425* (2013.01); *G01N 15/1459* (2013.01); *G05D 7/0658* (2013.01); *G01N 2015/1406* (2013.01); *G01N 2015/149* (2013.01)

(58) Field of Classification Search
USPC .......................................................... 382/103
See application file for complete search history.

(56) References Cited

U.S. PATENT DOCUMENTS

| | | | | | |
|---|---|---|---|---|---|
| 5,153,722 | A | * | 10/1992 | Goedeke | ................ H04N 7/18 169/61 |
| 6,549,130 | B1 | * | 4/2003 | Joao | ..................... B60R 25/018 307/10.2 |
| 6,961,445 | B1 | * | 11/2005 | Jensen | ................. G08B 13/194 348/208.15 |
| 2005/0074153 | A1 | * | 4/2005 | Pedrizzetti | ............... A61B 8/08 382/128 |
| 2006/0209184 | A1 | * | 9/2006 | Chen | .................... G08B 17/125 348/61 |
| 2007/0296570 | A1 | * | 12/2007 | Barrieau | ................ G08B 17/10 340/525 |
| 2009/0092284 | A1 | * | 4/2009 | Breed | ..................... B60J 10/00 382/103 |
| 2014/0334674 | A1 | * | 11/2014 | Lorenzoni | ............ G08B 17/125 382/103 |

* cited by examiner

*Primary Examiner* — Alex Liew
(74) *Attorney, Agent, or Firm* — Fox Rothschild LLP

(57) ABSTRACT

A modular monitor and control system which monitors the fluid jet and droplet formation region in a stream-in-air cell or particle sorter and controls sheath fluid and sample flows via the first and second valves. The system includes a processor which receives digital video image signals of the fluid jet and droplet formation region in the sorter; continuously analyzes the digital image signals to determine a significant change in the digital image signal; and triggers at least a relay switch activation signal in response to a determined significant change. At least one relay switch which is separate from the cell sorter and in communication with the processor is connected with the first and second valves and configured to close the first and second valves upon activation of the relay switch via the relay switch activation signal.

20 Claims, 3 Drawing Sheets

MODULAR MONITOR AND CONTROL SYSTEM FOR CELL SORTER STREAM

This application claims the benefit of U.S. Provisional Appln. No. 61/908,348, filed on Nov. 25, 2013, the contents of which are incorporated herein by reference.

FIELD OF THE INVENTION

This invention relates to stream-in-air small particle sorters. More specifically, the invention relates to a modular monitor and control system for stream-in-air cell sorters and other small particle sorters.

BACKGROUND OF THE INVENTION

Stream-in-air cell sorters are used in biomedical research and other fields to separate a mixture of cells or other small particles into various component types. They utilize a narrow stream of pressurized fluid ("sheath fluid") that is ejected from a nozzle as a jet and which carries within it the cells or particles held in suspension. The stream flows through the path of one or more light sources, the light from which may be scattered by the cells and which may stimulate fluorescent molecules associated with the cells. At the end of the fluid jet (droplet formation region), the jet breaks up into predictable, regularly-spaced droplets which are individually given an electrical charge, and which are then precisely deflected by an applied electric field, so that droplets containing single desired cells are directed into a designated collection receptacle. Thus, a highly purified subset of cells or particles with specific characteristics that are identifiable by specific fluorescent markers can be obtained.

Accurate cell sorting requires well-controlled and precise fluid dynamics of the jet and droplet formation region. Adverse events, like a partial blockage of the nozzle discharge orifice, an air bubble in the fluid stream, or an accidental change in instrument settings, can disrupt the normal fluid dynamics of the stream ("stream failure") and thereby interfere with proper sorting. This may result in a loss of desired cells and/or contamination of the collection receptacle(s) with unsorted cells, thereby ruining the purity of the sorted cells. To prevent or minimize this problem, the flow of the cell suspension sample and, if desirable, the flow of sheath fluid, must be interrupted as quickly as possible in the event of a stream failure. Some commercialized cell sorter models have automated this process as an integral part of their design, but many others have not. For the latter, the person operating the cell sorter must continuously monitor a live magnified video image of the stream and droplet formation region and be ready to react quickly to a stream failure by pressing a switch or the like to turn off the flow of cells and/or sheath fluid. The response of a human operator to a stream failure is limited by their ability to detect a change and by their reaction time, which may be exacerbated by inattention. Therefore, significant damage to the purity of the sorted cells may occur before a human operator can appropriately intervene. Also, continuous visual monitoring is a tedious and time-consuming task, since the operator must be constantly vigilant during the entire sorting time, often for many hours. Therefore, there is a need for a modular stream-monitoring and response system that can be utilized with steam-in-air sorters that do not incorporate such technology in their design.

SUMMARY OF THE INVENTION

Briefly, the present invention provides a modular device that continuously monitors the fluid jet and droplet formation region for potential changes and, in case of a stream failure, will automatically trigger certain action signals. The action signals can be configured to 1. Stop the flow of cell suspension "sample"), 2. Stop the flow of sheath fluid, 3. Trigger an audible alarm and/or visual warning on a computer screen, and 4. Send a warning email or text message. Thus, this system will immediately warn of a stream failure and prevent or minimize any potential contamination of the sorted cells by shutting off the flow of sample and/or sheath fluid, all within a fraction of a second, much quicker than a human operator could react manually. In essence, it will save the cell sorting process from being ruined by a stream failure. Importantly, it will also free the operator from the monotonous task of continuously visually checking the video image, allowing him/her to leave the sorter unattended for extended periods during ongoing cell sorting. This invention is adaptable to many different models of stream-in-air cell or particle sorters and does not interfere with the general operation of the sorter.

BRIEF DESCRIPTION OF THE DRAWINGS

The accompanying drawings, which are incorporated, herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1:
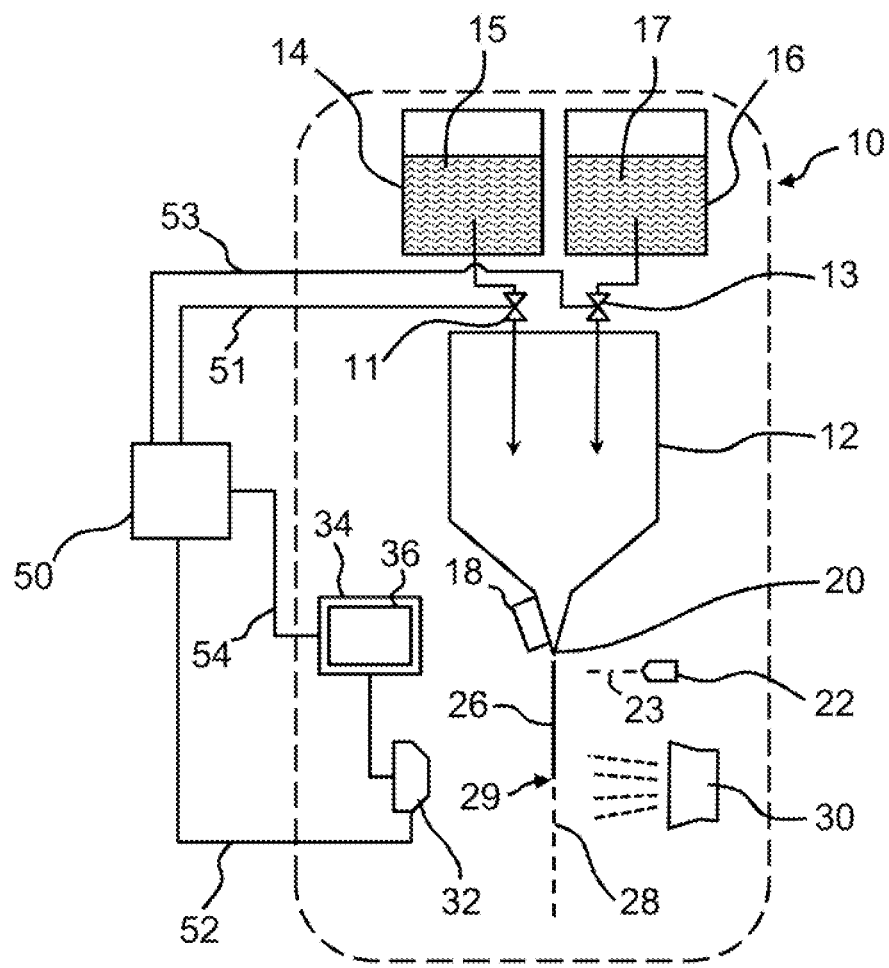
FIG. 1 is a schematic diagram of a modular monitor and control system in accordance with an exemplary embodiment of the invention connected to an exemplary cell sorter.

In the drawings, like numerals indicate like elements throughout. Certain terminology is used herein for convenience only and is not to be taken as a limitation on the present invention. For example, the terms front, back, left, right, above and below are utilized herein to assist with understanding of relative positioning, but are not intended to be limiting to an orientation of use of the device. The following describes a preferred embodiment of the present volition. However, it should be understood, based on this disclosure, that the invention is not limited by the preferred embodiment described herein.

Figure 2:
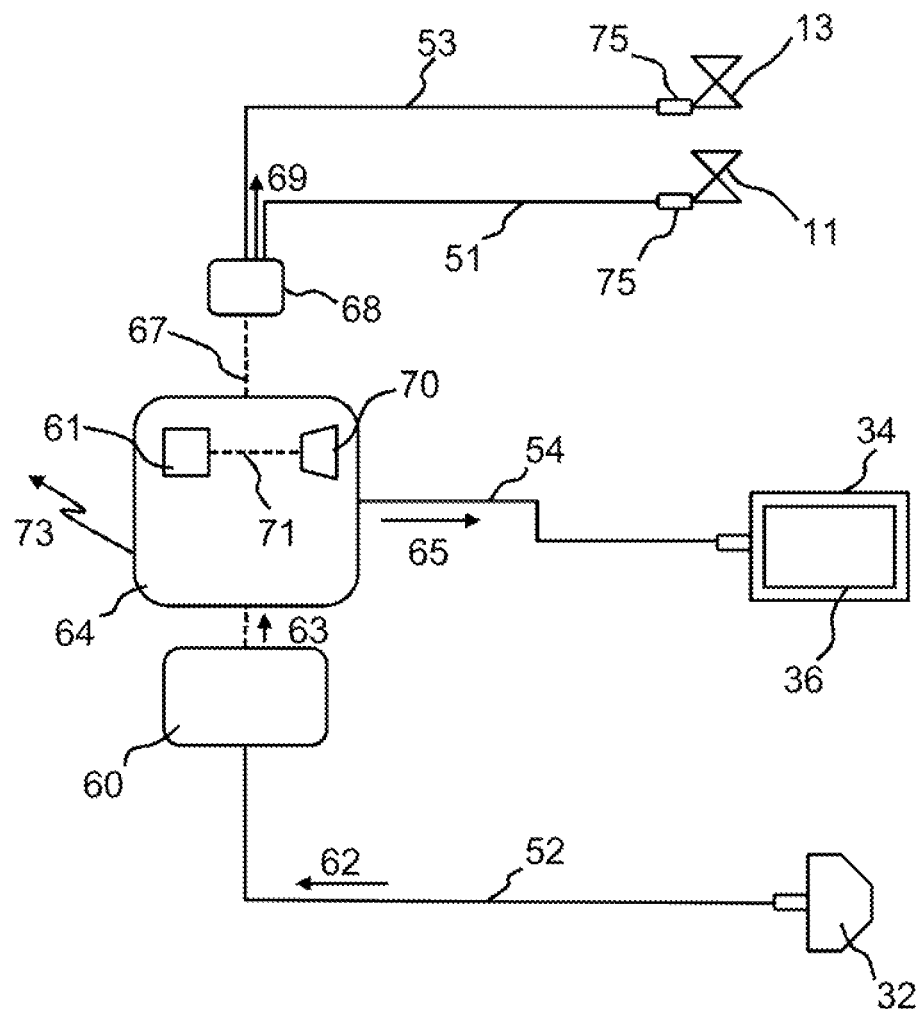
FIG. 2 is a schematic diagram of the modular monitor and control system of FIG. 1.

Referring to FIGS. 1-2, an exemplary embodiment of a modular monitor and control system 50 in use with a cell sorter 10 will be described. While the invention is described herein with respect to a cell sorter, the invention is not limited to such and may be utilized with other devices that sort any kind of small, particles, and which utilize similar technology as a stream-in-air cell sorter. The cell sorter 10 includes a nozzle 12 which receives a sample 15, with a suspension of cells or particles therein, from a sample reservoir 14 and combines it with a sheath fluid 17 received from a sheath fluid reservoir 16. A first control valve 11 is positioned between the sample reservoir 14 and the nozzle 12 and controls the flow of the sample 15. Similarly, a second control valve 13 is positioned between the sheath fluid reservoir 16 and the nozzle 12 and controls the flow of the sheath fluid 17. Control valves 11 and 13 may be operated electrically, or by pressure from air or other fluid supplied by actuator valves that are electrically operated.

The combined sample 15 and sheath fluid 17 are pressurized and flow through the nozzle 12 toward a small exit orifice 20 of a size from a few micrometers up to several millimeters in diameter. Prior to or after leaving the exit orifice 20, the combined fluid stream is subjected to light 23 from one or more light sources 22, as is known in the art. Suitable light sources include, without limitation, arc lamps, lasers, incandescent or fluorescent lamps, light emitting diodes (LED), among others. Preferably, the light sources 22 emit at a particular wavelength or spectrum of wavelengths, which includes, without limitation, those in the ultraviolet, visible, and infrared region, among others. Typically, the light source(s) 22 operate in a continuous node. In embodiments in which fluorescent (or other) dyes are incorporated into the sample, the light source(s) 22 can excite the dye molecules, both those bound to the particles and unbound, such that the dye molecules fluoresce at known wavelengths. The scattered light and fluorescence emissions due to passing particles in the illumination area are then quantified by detectors (not shown).

The combined sample and sheath fluid stream exits through the nozzle orifice 20 under pressure and at high speed as a jet 26, preferably in a steady-state flow. A droplet generator 18 is associated with and vibrates the nozzle 12 causing the end of the fluid jet to break up into predictable, regularly-spaced, uniform droplets 28 at a droplet formation region 29 located at a stable distance from the nozzle orifice 20. The droplet generator 18 may be in the form of a piezoelectric crystal or any other known vibration generating device.

An image capture device is provided to capture an image of the end of the continuous jet 26 and the droplets 28 below the nozzle 12. The imaging means can be located in a variety of positions to capture one or more views of the continuous jet 26 and droplets 28, but is preferably located at the droplet formation region 29. A variety of imaging means are known in the art and can be utilized in the present invention and include the imaging means described herein. For example, the image capture device may include a light source 30, e.g., LED lamp or other source, positioned on one side of the jet 26 and a video camera 32 positioned on the opposite side of the jet from the illumination. Preferably, the imaging means does not interfere with the signals received by the detectors from the illuminated particles.

When the light source 30 illuminates the jet 26 below the nozzle 12, it strobes light at a frequency that is the same as the frequency of the droplet generator 18. As a result, the jet 26 and droplets 28 appear as a still image, as seen by the video camera 32, where in reality droplets are constantly breaking off from the end of the jet and continue moving away from the nozzle.

The video camera 32 may be, for example, a charge coupled device (CCD), a video camera, or other analog or digital devices known for such image capture. The camera 32 collects the light from the light source 30, which is interrupted by the jet 26 and droplets 28 and thereby captures a live image of the droplet formation region 29. The image signals are that sent to a computer display monitor 36 for viewing by the operator.

The components and operation described with respect to the cell sorter 10 are typical of prior art cell sorters which do not have automated monitoring. Many commercially available cell sorters lack automated monitoring, for example, the BD Biosciences Influx, FACSJazz and FACSVantage SE. For cell sorters that have automatic monitoring, the technology is integrated into the design of the cell sorter and its operating software, and typically it is not adaptable to other instruments.

To provide automatic monitoring and control of the flow stream, a modular monitor and control system 50 in accordance with an exemplary embodiment of the invention is connected with the cell sorter 10 as illustrated in FIG. 1. The exemplary modular monitor and control system 50 receives image signals 62 from the camera 32 via a communication line 52, communicates with the processor 34 via a communication line(s) 54, and communicates with the first and second control valves 11 and 13 via communication lines 51 and 53, respectively. The information and function of the communications will be described in more detail below. While the exemplary embodiment is illustrated with hardwired communication lines 51, 52, 53 and 54, it is understood that wireless communication means, for example, RF, wifi, or Bluetooth™ communication means, may be utilized in place of any of the communication lines 51, 52, 53, 54.

The exemplary modular monitor and control system 50 is illustrated in FIG. 2 and further includes an analog-to-digital (A/D) video converter 60, a processor 64 and one or more relay switches 68. The A/D video converter 60 receives image signals 62 from the camera 32 via connection line 52. In most cases, the image signals 62 are in analog form, and the A/D video converter 60 converts the image signals 62 into digital image signals 63 which are then sent to the processor 64. In the event the image signals 62 are digital, the A/D video converter 60 can be configured to allow the signals to bypass it without conversion, or alternatively, the A/D video converter may be omitted. An exemplary A/D video converter 60 is "USB-Live 2", available from Hauppauge Computer Works, Hauppauge, N.Y.

The processor 64 is configured to run software and execute commands. The processor 64 may be in the form of a desktop or laptop computer, a tablet, a PDA, a smartphone, or any other appropriate computing device. The processor 64 has software 61 installed thereon configured to detect changes in the digital image signals 63, in an exemplary embodiment, the software 61 is motion-detection video monitoring software, which is also known as motion detection software. An exemplary motion-detection video monitoring software is "WebCam Monitor," available from Deskshare, Inc., Plainview, N.Y. The motion-detection software 61 continuously monitors the digital image signals 63 during operation of the cell sorter 10 and analyzes them fix any changes. That is, the motion-detection software 61 compares current image signals to preceding image signals and analyzes the signals to detect any changes therebetween. If a change in image signals is sufficiently large, such as with an acute stream failure, the software 61 will immediately trigger one or more signals to indicate such a disruption. The software 61 may additionally be configured to detect smaller gradual changes over an extended time, i.e. cumulative changes. In one embodiment, the software 61 may be configured to capture an initial image signal and then compare the current image signals to the initial image signal such that the software 61 responds to cumulative changes as well as acute changes that exceed a certain threshold. The operator may be provided with the capability to change modes such that the software responds to acute changes only or to both cumulative and acute changes. Additionally, while motion-detection software is described in conjunction with the exemplary embodiment, other types of software may be utilized to analyze the digital image signals 63 and detect changes therebetween.

If a sufficiently large change in image signals is detected by the software 61, a first signal 71 may be provided to the processor 64 whereby an audible alarm, corresponding to a selected audio file stored on the processor's memory, is output by a speaker 70 or the like of the processor 64. A second signal may be a message signal 65 provided to the cell sorter processor 34 whereby a message to the operator is shown on the computer display monitor 36. Alternatively, or additionally, remote message signals 73 may be generated whereby an email, text message or other remote message is sent to one or more designated individuals. A third signal 67 is sent to trigger operation of the relay switches 68 as will be described below. The threshold for the magnitude of image signal change required to trigger a response by the software can be adjusted by the operator, and any compatible audio file can be utilized for the audible alarm.

The relay switches 68 are preferably provided in a multiple-channel relay switch in which each channel is a separate circuit that is independently controlled, as illustrated in the Figures, however, separate relay switches 68, each with a single circuit, may be utilized. The relay switches 68 are configured to close the valves 11 and 13 that control the flow of the sample 15 and sheath fluid 17, respectively, when the activation signal 67 is received. When activated, one or more of the switches 68 opens, thus interrupting electrical current to either one or both of the valves 11 and 13, allowing the valves 11 and 13 to close and stop the respective flows. Each of the two valves 11 and 13 is independently controlled by the relay switches 68 according to settings in the software 61 at the discretion of the operator. In the event valves 11 and 13 are operated by pressure from air or other fluid, then the relay switches 68 can be configured to control the corresponding electrical actuator valves instead. Electrical wiring harnesses 75 with compatible connectors are preferably configured to connect the switches 68 to the valves 11 and 13 and their respective electrical power sources in the cell sorter 10 without harming extant electrical wires of the cell sorter 10.

Software-based button icons are displayed on the computer display monitor 36 and can be activated by the operator to send a command to the processor 64 to reset the relay switch 68 to the normally-closed position and thereby restore normal valve function after the triggering event has been resolved. The relay switches 68 preferably include latching, switches that remain in their last state until commanded to switch states. The commands to open or close the relay switches 68 are part of a software module in the processor 64 that is activated by the motion-detection video monitoring software 61 and is independent of the cell sorter operating software. The relay switches 68 may require a software-based driver, for example, provided by the manufacturer, which can be installed on the processor 64. An exemplary relay switch 68 is the DLP-IOR4 USB 4-channel relay; available from DLP Design of Allen, Tex. The A/D converter 60 and the relay switches 68 may communicate with the processor 64 via USB connectors or any other wired or wireless means.

Figure 3:
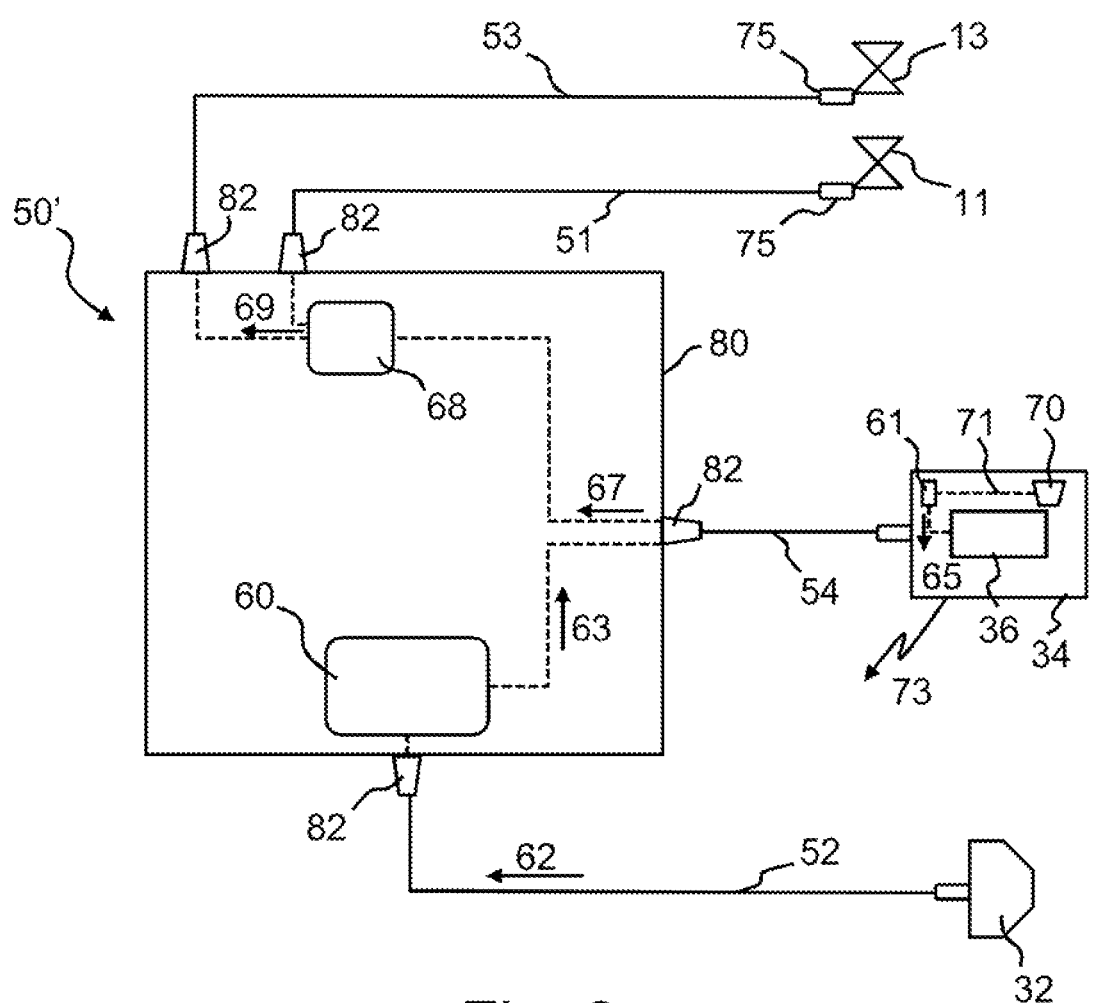
FIG. 3 is a schematic diagram of a modular monitor and control system in accordance with another exemplary embodiment of the invention.

Referring to FIG. 3, a modular monitor and control system 50' in accordance with another exemplary embodiment of the invention will be described. The system 50' is similar to the previous embodiment, but does not include an independent processor, but instead utilizes the cell sorter's processor 34. While the cell sorter's processor 34 is utilized, the motion-detection video monitoring software 61 is installed on the processor 34 such that it functions independently of the cell sorter 10 software. As illustrated, the same signals 62, 63, 65, 67, 69, 71 and 73 are processed in the same manner as in the previous embodiment and the system 50' operates in the same manner as described above.

The system 50' includes a housing 80 or the like in which the A/D converter 60 and the relay switches 68 are housed. Connectors 82 on the housing 80 facilitate connection of the A/D converter 60 and the relay switches 68 with the various communication lines 51, 52, 53, 54. While not shown, it is understood that the previous embodiment can include a housing which contains the A/D converter 60, the relay switches 68 and the processor 64.

The system 50, 50' of the present invention can be added to stream-in-air cell sorters 10 to monitor the jet and droplet formation region and automatically respond to a stream failure by immediately shutting off the flows of sample and sheath fluid to prevent contamination of the collection receptacles with unsorted cells. The system 50, 50' functions independently of the sorter operating software and interfaces with the cell sorter 10 only via its connections to valves 11 and 13 using a simple electrical wire harness. The normal operation of these valves is unaffected when the respective relay switches are in their normally-closed positions, such as when the system has not responded to a stream failure. Therefore, the system does not interfere with the usual operation of the cell sorter's operating software or the sorter instrument 10.

The system's audible alarm, visual warning message, and remote electronic messaging capability provide notification that a problem has been detected and flow has been stopped. Thus the operator can receive notification of the problem even if he/she happens to be away from the sorter. The operator can then respond as necessary, but without need for urgency since the flows of sheath fluid and sample will already have been stopped, thus preventing contamination of the sorted cells with unwanted cells. The warning methods are configurable by the operator.

The stream-monitoring and response system described also displays the live video image of the droplet formation region on the computer display monitor 36 of the cell sorter's processor. Since stream droplet break-off dynamics may change slowly over time in any cell sorter, this can help the operator to maintain proper stream droplet formation by allowing the operator to compare the live video image of the stream to a still image of an optimal stream and droplet formation which can be displayed adjacent to the live video image. These two images positioned side-by-side facilitate the visual detection of any small, incremental changes in the stream that otherwise might go unnoticed by the operator. The operator can then make appropriate adjustments to the instrument settings to maintain optimal stream conditions before the gradual changes accumulate to the point of affecting sorting accuracy. An image of the optimal jet and droplet formation region to be used for comparison can be created by the operator by capturing a still image from the monitored video image after the instrument is properly set up and before beginning the sort process.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as defined in the claims.

What is claimed:

1. A modular monitor and control system configured to monitor the fluid jet and droplet formation region in a stream-in-air particle sorter and control flows of sheath fluid and particle suspension sample via first and second valves, the system comprising:

a processor configured to: receive digital video image signals of the fluid jet and droplet formation region in the sorter; continuously analyze the digital video image signals to determine a significant change in the digital image signal; and trigger an alert signal in response to a determined significant change, the alert signal including at least a relay switch activation signal; and at least one relay switch separate from the particle sorter and in communication with the processor, the at least one relay switch connected with the first and second valves and configured to close the first and/or second valve upon activation of the at least one relay switch via the relay switch activation signal.

2. The modular monitor and control system of claim 1 further comprising an analog-to-digital video converter separate from the sorter and configured to receive an analog signal of a video image of the fluid jet and droplet formation region in the sorter and convert it into the digital signal received by the processor.

3. The modular monitor and control system of claim 1 wherein the processor runs motion-detection video monitoring software to analyze the digital video image signals and determine a significant change in the digital image signal.

4. The modular monitor and control system of claim 1 wherein the processor is configured to compare current image signals to preceding image signals and/or compare current image signals to an initial image signal and analyzes the signals to detect any changes therebetween beyond a threshold value.

5. The modular monitor and control system of claim 4 wherein the threshold value is adjustable.

6. The modular monitor and control system of claim 4 wherein an operator can select between comparing the current image signals to the preceding image signals or the initial image signal.

7. The modular monitor and control system of claim 1 wherein the processor is an independent component relative to the particle sorter and is configured to receive video image signals therefrom via a wired or wireless connection.

8. The modular monitor and control system of claim 1 wherein the processor is an integral component of the particle sorter and software, independent of software configured to control operation of the particle sorter, is configured to continuously analyze the digital video image signals to determine a significant change in the digital image signal and trigger an alert signal in response to a determined significant change.

9. The modular monitor and control system of claim 1 wherein the alert signal further includes an alarm signal configured to cause an audible alarm.

10. The modular monitor and control system of claim 1 wherein the alert signal further includes a message signal configured to cause a visual message to be displayed on a display monitor.

11. The modular monitor and control system of claim 1 wherein the alert signal further includes a remote message signal configured to cause a warning message to be sent to a remote location.

12. The modular monitor and control system of claim 1 wherein the at least one relay switch is a multiple-channel relay switch, with one channel associated with the first valve and one channel associated with the second valve and with ability to control each channel independently.

13. The modular monitor and control system of claim 1 wherein the at least one relay switch includes two independent relay switches, with one of the relay switches associated with the first valve and the other relay switch associated with the second valve.

14. The modular monitor and control system of claim 1 wherein the first and second valves are electrically operated and the at least one relay switch is electrically connected to the first and second valves.

15. The modular monitor and control system of claim 1 wherein the first and second valves are fluidly activated by third and fourth valves which are electrically operated and the at least one relay switch is electrically connected to the third and fourth valves.

16. The modular monitor and control system of claim 1 wherein the at least one relay switch includes latching switches which remain in a current state until commanded to switch states.

17. The modular monitor and control system of claim 16 further comprising an input which allows an operator to return the latching relay switches to a state in which control of the first and second valves is returned to the particle sorter and operator.

18. The modular monitor and control system of claim 1 further comprising a housing in which at least the at least one switch is positioned.

19. The modular monitor and control system of claim 18 wherein an A/D converter is positioned within the housing.

20. The modular monitor and control system of claim 18 wherein the processor is positioned within the housing.

* * * * *